United States Patent [19]
Green

[11] Patent Number: 5,696,046
[45] Date of Patent: Dec. 9, 1997

[54] COLD STERILANT SOLUTION

[76] Inventor: Bruce Philip Green, Winwick Hall, Northampton, Northampton NN6 7BP, England

[21] Appl. No.: 708,900

[22] Filed: Sep. 5, 1996

Related U.S. Application Data

[63] Continuation of Ser. No. 333,431, Nov. 2, 1994.

[30] Foreign Application Priority Data

Oct. 6, 1994 [GB] United Kingdom ............... 9420201

[51] Int. Cl.$^6$ .......................... C11D 3/20; C11D 3/48
[52] U.S. Cl. .................. 502/161; 502/245; 502/255; 502/379
[58] Field of Search .................... 510/161, 245, 510/254, 255, 370, 379

[56] References Cited

U.S. PATENT DOCUMENTS

| | | | |
|---|---|---|---|
| Re. 31,779 | 12/1984 | Alliger .................. | 252/187.23 |
| 2,379,335 | 6/1945 | Mountclair . | |
| 2,575,670 | 11/1951 | MacMahon . | |
| 3,585,147 | 6/1971 | Gordon . | |
| 3,873,696 | 3/1975 | Randeri et al. . | |
| 4,201,756 | 5/1980 | Saeman et al. . | |
| 4,296,102 | 10/1981 | Laso . | |
| 4,296,103 | 10/1981 | Laso . | |
| 4,317,814 | 3/1982 | Laso . | |
| 4,330,531 | 5/1982 | Alleger . | |
| 4,507,285 | 3/1985 | Kuhne . | |
| 4,880,638 | 11/1989 | Gordon . | |
| 5,077,008 | 12/1991 | Kralovic et al. .......... | 422/37 |
| 5,116,575 | 5/1992 | Badertscher ............ | 422/28 |
| 5,165,910 | 11/1992 | Oikawa et al. .......... | 423/477 |
| 5,217,698 | 6/1993 | Siegel et al. ........... | 422/295 |
| 5,352,383 | 10/1994 | Johnson et al. ........ | 252/389.62 |

FOREIGN PATENT DOCUMENTS

| | | |
|---|---|---|
| 9420201 | 11/1994 | United Kingdom . |
| WO 85/04107 A1 | 3/1984 | WIPO . |
| 04107 | 9/1985 | WIPO . |
| 85/04107 | 9/1985 | WIPO . |
| WO 91/03265 A1 | 3/1991 | WIPO . |

OTHER PUBLICATIONS

J.C. Hoff and E. Geldreich, "Comparisons Of The Biocidal Efficiency Of Alternative Disinfectants", Proceedings AWWA Seminar on water disinfection with ozone, chloramines or chlorine dioxide, Jun. 1980, pp. 39–49.

J.R. Lubbers and J.R. Blachine, *Effects of Acute Rising Dose Administration of Chlorine Dioxide, Chlorate and Chlorite to Normal Healthy Male Volunteers*, J. Environ. Pathol. Toxicol. and Oncology, 5:215–218, Jul. 1984.

Appelton H., "Foodborne Illnesse", The Lancet Dir. 1991, 336:1362–4. No month.

Association of Official Analytical Chemists, 1980. Disinfectants. In: Official Methods of Analysis, 13th ed. (Horowitz W., ed.), pp. 56–68. Association of Official Analytical Chemists. Washington, D.C. No month/1980.

E.M. Aieta and J.D. Berg, "A Review of Chlorine Dioxide in Drinking Water Treatment", Ournal AWWA vol. 78, No. 6, Jun. 1986, pp. 62–76.

Aieta, E.M., et al., "Determination of Chlorine Dioxide, Chlorine, Chlorite and Chlorate in Water", Journal AWWA, vol. 76, No. 1, Jan. 1984, pp. 14–70.

Hong D.C. & Rapson, "W.H. Analyses of Chlorine Dioxide, Chlorous Acid, Chlorite, Chlorate and Chloride in Composition Mixtures", Can. Jour. Chem., 46:2061 (1968). No month.

Columnbia Dept. of Chemistry, "Progress in Inorganic Chemistry", vol. 15, 1972. No month.

*Primary Examiner*—Glenn A. Caldarola
*Assistant Examiner*—Alexander G. Ghyka
*Attorney, Agent, or Firm*—Merchant, Gould, Smith, Edell, Welter & Schdmit, P.A.

[57] ABSTRACT

A sterilant-disinfectant solution which may be used in the cleaning of metallic objects, particularly medical instruments. Medical instruments, which may include brass, copper, aluminium, stainless steel, carbon steel or plastic parts are sterilized or disinfected in an anti-microbial solution. The solution includes a triazole or other component for inhibiting the corrosion of copper and brass. Phosphates or other buffering agents adjust the solution pH in order to prevent the corrosion of steel. Molybdates or analogous compounds may be used to buffer the pH and have been found to inhibit the corrosion of aluminium by oxidizing agents. A sequestering agent is preferably provided for inhibiting hard water precipitation.

11 Claims, No Drawings

COLD STERILANT SOLUTION

This is a Continuation of application Ser. No. 08/333, 431, filed Nov. 2, 1994.

The present invention relates to a sterilant-disinfectant solution which may be used in the cleaning of metallic objects, particularly medical instruments. Medical instruments, which may include brass, copper, aluminium, stainless steel, carbon steel or plastic parts are sterilized or disinfected in an anti-microbial solution. The solution includes a triazole or other component for inhibiting the corrosion of copper and brass. Phosphates or other buffering agents adjust the solution pH in order to prevent the corrosion of steel. Molybdates or analogous compounds may be used to buffer the pH and have been found to inhibit the corrosion of aluminium by oxidizing agents. A sequestering agent is preferably provided for inhibiting hard water precipitation.

BACKGROUND OF THE INVENTION

In medical diagnosis and therapy, open surgical operations are being replaced to an increasing extent by the use of endoscopes. However, flexible glass fibre endoscopes become massively infected with microorganisms which are present in body cavities, on the mucous membrane, and in the blood. Accordingly, used endoscopes have to be thoroughly cleaned and disinfected after each use.

Glass fibre endoscopes are extremely complicated precision instruments which have moving parts and which are made from a number of materials. They are extremely difficult to clean and disinfect for a number of reasons. Not only the outer surfaces of the instrument, but also the narrow bores present in the interior have to be cleaned and disinfected. In view of the sensitivity of the materials involved, cleaning and disinfection have to be performed in such a way that no residues of the preparation used remain on the treated surfaces of the instrument. The extremely effective process of thermal sterilization normally used for medical instruments cannot be applied to endoscopes because endoscopes are made partly of temperature-sensitive materials. Another factor to be taken into consideration is that many of the metal parts present are susceptible to corrosion. Finally, endoscopes should be able to be cleaned and disinfected in a short time so that they are always ready in good time for the treatment of the next patient.

While the process of the invention has particular application to endoscopes, the process can be used to clean and sterilize other surgical, medical, or dental devices and equipment, or in fact any equipment or devices having hard surfaces for any use where cleaning and disinfecting such hard surfaces is desired, particularly equipment and devices that cannot tolerate high temperature cleaning and sterilization.

CHLORINE DIOXIDE AS STERILANT

Chlorine dioxide is an extremely effective sterilant and bactericide, equal or superior to chlorine on a mass dosage basis. Its efficacy has been well documented in the laboratory, in pilot studies and in full-scale studies. Unlike chlorine, chlorine dioxide does not hydrolyse in water. Therefore, its germicidal activity is relatively constant over a broad pH range.

At pH 6.5, doses of 0.25 mg/l of chlorine dioxide and chlorine produce comparable one minute kill rates for the bacterium *Escherichia coli*. At pH 8.5, chlorine dioxide maintains the same kill rate, but chlorine requires five times as long. Thus, chlorine dioxide should be considered as a primary sterilant in high pH, lime-softened waters.

Chlorine dioxide has also been shown to be effective in killing other infectious bacteria such as *Staphylococcus aureus* and Salmonella. Chlorine dioxide is as effective as chlorine in destroying coliform populations and is superior to chlorine in the treatment of commonly found viruses. In a test, Poliovirus 1 and a native coliphage were subjected to these two disinfectants. A 2 mg/l dose of chlorine dioxide produced a much lower survival rate than did a 10 mg/l dose of chlorine.

A sterilant must provide specified levels of microorganism kills or inactivations as measured by reductions of coliforms, heterotrophic plate count organisms and Legionella bacteria. Disinfection is currently defined by the Environmental Protection Agency to mean 99.9 per cent reduction in the *Giardia lamblia* cyst levels and 99.99 per cent reduction in enteric virus concentrations. Disinfection is expressed as a CT. value (i.e. a function of Concentration× Contact Time). At the CT values necessary for chlorine dioxide to inactivate 99.9 per cent of *Giardia lamblia* cysts, the simultaneous inactivation of 99.99 per cent of enteric viruses is also assured.

ACTIVATING ACID

Although chloride dioxide has been found to be an excellent sterilant, it is difficult to use in direct form. In gaseous state, chloride dioxide is explosive and poisonous. Accordingly, sodium chlorite is used as a chloride dioxide-liberating material. Chloride dioxide may be liberated from the sodium chlorite (or any other suitable liberating material) by the addition of a suitable activating system, most usually an acid. Various inorganic and organic acids have been tested as activating systems. A description of the various acid systems which may be used is given in EP-A-0176558 (Alcide Corporation). Preferred acids are lactic acid, phosphoric acid, acetic acid, sorbic acid, ascorbic acid, phosphoric acid and hydrochloric acid. It is preferred that the acid should be present in an amount from 0.01 to 10% based on the total weight of the composition. Citric acid is a preferred acid for use in activation. Combinations of suitable acids may be used, e.g. a combination of sorbic, boric and citric acid. Such a combination is preferred as the sorbic and boric acid act not only as activators but also as bactericides in their own right. A higher "kill" is found than if using citric acid alone or in combination with, for example, lactic acid.

CORROSION INHIBITION

Many liquid sterilization systems are highly corrosive to metal parts, particularly brass, copper, and aluminium. With long immersion times, even carbon steel and stainless steel could be pitted and sharp cutting edges dulled.

The use of a simple sodium chlorite/acid activator system as a sterilizer of various instruments leads to corrosion of metal parts, due to the aqueous basis of the system. The corrosion means that expensive instruments have a shortened lifetime.

A number of corrosion inhibitors are available and are well-known. However, if an oxidizing agent, for example chlorine dioxide, is to be used as the sterilizing agent, various problems must be overcome in selecting suitable inhibitors. The main problem is that the inhibitors must be effective in powerful oxidizing solutions where chloride ions are present. Furthermore, the inhibitors must be stable under long-term storage in acidic conditions, and must not react together to form deposits or harmful reaction products. The inhibitors should not present a health hazard, either when left in trace quantities on the sterilized instruments or prior to use.

The cleaning environment also produces special problems. The oxygen liberating agent is acidic. Because a number of different metals may be in the sterilizing tank at the same time, galvanic corrosion may be initiated. There is a need to overcome this.

In accordance with the present invention, a new and improved anti-microbial composition is provided which overcomes the over problems. An anti-microbial solution is provided which comprises an oxidizing anti-microbial agent, a copper and brass corrosion inhibitor and buffering agent, a wetting agent and sequestering agent.

The oxidizing anti-microbial agent can be selected from the class consisting of ozone, peracetic acid, organic peroxides, hydrogen peroxides, inorganic peroxides, and other oxygen releasing compounds, chlorine, chlorine dioxide, active chlorine releasing compounds such as chloramines, hypochlorites and phenol.

The copper and brass corrosion inhibitor is selected from the class consisting essentially of triazoles, azoles, benzoates, and five membered ring compounds. Triazoles, particularly benzotriazole and tolytriazole are preferred as being stable in the presence of strong oxidizing compounds. Benzotriazole is most preferred as it also helps to prevent galvanic corrosion in mixed metal systems. Mercaptobenzathiozal might also be utilized but may be destabilized by strong oxidizers. They might be present at 0.01 to 2.0 wt. % of the sterilizer system.

The aluminium and steel corrosion inhibitor and the buffering agent may be selected from the class consisting essentially of chromates, dichromates, borates, nitrates, phosphates, molybdates, vanadates and tungsdates. More specifically to the preferred embodiment, phosphates are preferred of inhibiting steel corrosion and buffering the solution. Molybdates are preferred for inhibiting aluminium corrosion and nitrates, particularly sodium nitrate, for inhibiting steel and ferric corrosion.

The anti-corrosive buffering compounds may include a mixture of phosphate in sufficient volume to produce a final concentration of 1.25 weight per Volume and molybdates in an appropriate amount to produce a final solution of 0.11% weight per volume. Phosphates may also be effective in the range of 0.2% to 12% and the molybdates may be effective from 0.1% to 10%. Optionally, chromates, dichromates, tungstates, vanadates, other borates, and combinations thereof may be substituted in appropriate concentrations to inhibit steel corrosions and aluminium corrosion.

Amines are often used as corrosion inhibitors. However, amine derivatives were rejected because of unpredictable film forming properties.

In hard water, calcium and magnesium salts can precipitate and coat the instruments being sterilized. A sequestering agent appropriate to prevent precipitation, such as sodium hexametaphosphate, may be provided; if deionized or soft water is utilized the sequestering agent may be eliminated. However, to ensure universal applicability with any water that might be utilized, the presence of a sequestering agent is preferred. It has been found that sodium citrate and trisodium phosphate also act as sequestering agents.

A wetting agent present from 0.1 to 100 wt. %, preferably 1.0 to 5.0 wt. %, improves the wetting of the surface of the instrument by the anti-microbial agent. The wetting agent has also been found to increase penetration of the anti-microbial improving anti-microbial efficacy while reducing corrosion. Defoamers and preservatives may also be included, at levels of 0.01 to 1 wt. %.

EXAMPLE 1

Effect of Activating Acid

The possible contribution of acid used to activate (base) sodium chlorite (convert the stabilised chlorine dioxide into free chlorine dioxide) towards the biocidal activity of chlorine dioxide has been investigated. *Listeria monocytogenes* ATCC 15313 was used as the test organism to eliminate acid sensitivity (characteristic of some gram negative eubacteria such as *Pseudomonas aruginos*) as an experiment variable. *L. monocytogenes* was grown on a modified synthetic broth as described in A.O.A.C. Methods amended by the addition of Soytone, 3 g/liter, to support growth.

Cultures were incubated for 24 hours at 37° C.

The acids tested are tabulated below. HCl was selected as a strong inorganic acid. Phosphoric acid, $H_3PO_4$ was selected as another inorganic acid and was selected because of its common use in dairy processing plants. Lactic acid was chosen because claims have been made that lactic acid contributes to the anti-microbial activity of the product. Citric acid is another organic acid and is the acid used to activate the stabilised chlorine dioxide for its use as a germicide/disinfectant. Ascorbic acid is a third organic acid which is also a mild reducing agent; it was tested to determine if the combination of a reducing agent with the oxidising chlorine dioxide would still be biocidal or be more active than chlorine dioxide alone. A combination of sorbic acid, boric acid and citric acid was also used because of their antimicrobial activity, and was found to be particularly effective.

Sodium chlorite was activated as follows: 2× of the normal level of activating acid was added to a 100 ml graduated cylinder. 5.0 ml sodium chlorite solution was added. After 2 minutes the solution was diluted to 100 ml with deionized water, yielding a 1,000 ppm (calculated) stock of chlorine dioxide.

1.0 ml of culture of *L. monocytogenes* was added to synthetic hard water, 100 ppm hardness, and chlorine dioxide was added at 25 and 50 ppm (calculated) to initiate the test. The test volume was 50 ml.

Time points were taken at 30 and 60 seconds by adding 1.0 ml of a test to 4.0 ml of sodium thiosulfate (2,000 ppm). This was serially diluted and plated for enumeration in the original growth medium containing 10 g/liter purified agar. Viable cell counts were determined after 48 hours of incubation at 37° C.

Results

After activation, the levels of chlorine dioxide were compared by eye and were: HCl>$H_3PO_4$>lactic acid=citric acid>ascorbic acid. The amount of chlorine dioxide formed was a function of the $pk_a$ of the activating acid and not the level of acid (in this experiment); an acid with a lower $pk_a$ produced more chlorine dioxide than an acid with a higher $pk_a$.

The antimicrobial activity was a function of the apparent level of chlorine dioxide formed upon activation. Thus, an activating acid with a lower $pk_a$, which produced more $ClO_2$, produced a solution with a greater level of biocidal activity. A combination of acid activators showed a synergistic effect, giving results as good as those produced by an activator with a lower $pk_a$.

EFFECT OF ACTIVATING ACID ON SODIUM CHLORITE SOLUTION

| Acid | ppm | Viable Cell Count/ml 30 seconds | 60 seconds |
|---|---|---|---|
| HCl | 25 | $3 \times 10^3$ | $<2 \times 10^6$ |
|  |  | $5 \times 10^6$ | $<2 \times 10^6$ |
| HCl | 50 | $<2 \times 10^6$ | $<2 \times 10^6$ |
|  |  | $<2 \times 10^6$ | $<2 \times 10^6$ |
| $H_3PO_4$ | 25 | $<2 \times 10^6$ | $<2 \times 10^6$ |
|  |  | $2 \times 10^2$ | $1 \times 10^1$ |
| $H_3PO_4$ | 50 | $<2 \times 10^6$ | $<2 \times 10^6$ |
|  |  | $<2 \times 10^6$ | $<2 \times 10^6$ |
| Citric acid | 25 | $5 \times 10^4$ | $3 \times 10^3$ |
|  |  | $4 \times 10^2$ | $4 \times 10^1$ |
| Citric acid | 50 | $3 \times 10^1$ | $8 \times 10^6$ |
|  |  | $6 \times 10^2$ | $4 \times 10^1$ |
| Ascorbic acid | 25 | $1 \times 10^7$ | $1 \times 10^7$ |
|  |  | $4 \times 10^7$ | $1 \times 10^7$ |
| Ascorbic acid | 50 | $3 \times 10^6$ | $4 \times 10^6$ |
|  |  | $4 \times 10^6$ | $4 \times 10^6$ |
| Sorbic acid |  |  | $<2 \times 10^6$ |
| Citric acid | 50 | $<2 \times 10^6$ |  |
| Boric acid |  | $<2 \times 10^6$ | $<2 \times 10^6$ |

Control: $6 \times 10^6$/ml *Listeria monocytogenes* ATCC 15313

EXAMPLE 2

Corrosion Inhibition

Endoscope Materials

Metallic components from the Olympus® endoscopes were used as test pieces. They comprised austenitic stainless steel (BS303,316), glass (Q2121) aluminium and two silicon-bearing aluminium alloys, A12011T3 and A16262T9 respectively. All of these materials are likely to be susceptible to attack by acid solutions of chloride ions, although there is little risk from $ClO_2$ itself.

Corrosion Test Procedure

The test involves imposing on the test specimen a steadily increasing aggressive potential and observing the resulting anodic current. (This is a potentiodynamic procedure.) Until active corrosion (pitting) occurs, low anodic currents allow some comparison of the respective stabilities of metallic components and the likelihood of galvanic effects. The potential corresponding to the establishment of pitting is a measure of the effectiveness of intrinsic passivity or of inhibition.

In practice, a single open cell is used which contains the test piece, suitably mounted as an electrode, a calomel reference electrode and an iridium counter electrode. The potential between the test electrode and the reference is monitored and controlled by a Solartron Instruments Electrochemical Interface (Type 1286) which supplies the measured and recorded corrosion current via the iridium counter counter electrode.

Test electrodes are immersed in the electrolyte until the open circuit potential stabilizes. The potential is then swept anodically until passivation for inhibition breaks down. It is an important feature of the experiment that the applied potential should change slowly (typically 0.5 mV sec$^{-1}$) to allow the surface phases to respond.

The cell was held at 20° C.

The electrolytes correspond to working biocidal solutions with or without inhibitor.

Results

Uninhibited Solution

Uninhibited electrolyte was harmless to the stainless steels but was aggressive towards brass and both pure aluminium and its two alloys. In practical use there would be a risk of contamination of stainless steel components with corrosion products (notably copper) from brass. This could lead to harmful galvanic effects. Aluminium and its two alloys did not withstand the solution without inhibitors.

It is unlikely that the test pieces would experience conditions in the field as aggressive as those which have produced failures in the laboratory, unless severely contaminated or held for unreasonably long periods in used biocide.

Inhibited Solution

Very good inhibition was expected and found on the stainless steels. There was a notable improvement in performance of brass in these electrolytes and this promises well for the behaviour of multi-metal articles. Excellent inhibition of aluminium was obtained.

The duration of the corrosion tests was longer than the recommended sterilizing time; immersions of 2 hours at the open circuit potentials were harmless to the test pieces. Potentials of metals (and potential differences) between metal components are unlikely to produce a corrosive effect greater than that corresponding to $-0.2V$ in the present experiments, so that a large "reserve" of corrosion resistance is provided by the inhibitor formulation.

Conclusion

It was concluded that the solution with inhibitor provided more than adequate protection of the metal parts from the biocide even when used for extended immersion periods, four times longer than recommended.

EXAMPLE 3

The following two-part sterilizing system was prepared:

|  |  | Wt %. |
|---|---|---|
| A | Sodium Chlorite Solution |  |
|  | 25% Sodium Chlorite Solution | 9.2 |
|  | Demineralized water | →100 |
| B | Acid Activator |  |
|  | Citric Acid | 6.0 |
|  | Sorbic Acid | 1.0 |
|  | Boric Acid | 1.0 |
|  | Sodium Citrate | 2.5 |
|  | Trisodium Phosphate | 2.5 |
|  | Benzotriazole | 0.1 |
|  | Sodium Molybdate | 0.5 |
|  | Sodium Nitrate | 2.0 |
|  | Defoamer, Wetting Agent, Preservatives | 1.5 |
|  | Demineralized Water | →100 |

The acid activator was added to the sodium chlorite solution to produce a sterilant system. The system was used to sterilize a number of test medical instruments, for example endoscopes. After repeated treatment, no corrosion was observed. In a comparative test, a non-inhibited system showed that pitting was developing on metal parts.

I claim:

1. A two-part sterilizing system comprising:
   (a) a first part comprising sodium chlorite solution; and
   (b) a second part comprising an organic acid and a corrosion inhibitor, said organic acid comprises citric acid, sorbic acid, and boric acid, and said corrosion inhibitor comprising a copper and brass corrosion inhibitor, a steel and aluminum corrosion inhibitor, and a buffering agent;

wherein said first part and said second part, when combined, provide a sterilizing composition having a pH of about 5.5 or higher.

2. A two-part sterilizing system according to claim 1, wherein the copper and brass corrosion inhibitor is a triazole or benzotriazole present in a weight percent of 0.01 to 2.0.

3. The two-part sterilizing system according to claim 1, wherein the steel and aluminum corrosion inhibitor is selected from the group consisting of phosphates, molybdates, and nitrates, and is present in a weight percent of from 0.01 to 5.0.

4. The two-part sterilizing system according to claim 1, further comprising a steel and ferric corrosion inhibitor comprising sodium nitrate.

5. The two-part sterilizing system according to claim 1, further comprising a sequestering agent.

6. The two-part sterilizing system according to claim 1, further comprising a wetting agent, a defoamer, or a combination thereof.

7. The two-part sterilizing system according to claim 1, wherein said buffering agent comprises trisodium phosphate.

8. A sterilizing composition comprising:

(a) sodium chlorite solution;

(b) an organic acid comprising citric acid, sorbic acid, and boric acid;

(c) a buffering agent comprising trisodium phosphate;

(d) a corrosion inhibitor comprising a copper and brass corrosion inhibitor, and a steel and aluminum corrosion inhibitor.

9. The composition according to claim 8, wherein said composition has a pH of about 5.5 or higher.

10. A method for sterilizing medical instruments, said method comprising:

(a) preparing a sterilizing composition by combining a first part comprising sodium chlorite solution, and a second part comprising an organic acid, a corrosion inhibitor, and a buffering agent, wherein the organic acid comprises citric acid, sorbic acid, and boric acid;

(b) introducing a medical instrument into the sterilizing composition to effect sterilization of the medical instrument.

11. The method for sterilizing medical instruments according to claim 10, further comprising a step of:

(a) adjusting the pH of the sterilizing composition to about 5.5 or higher.

* * * * *

UNITED STATES PATENT AND TRADEMARK OFFICE
CERTIFICATE OF CORRECTION

PATENT NO. : 5,696,046

DATED : DECEMBER 9, 1997

INVENTOR(S) : GREEN

It is certified that error appears in the above-identified patent and that said Letters Patent is hereby corrected as shown below:

Title page, [30] Foreign Data: "9420201" should read --9420201.7--

Col. 5, line 61: "for" should read --or--

Signed and Sealed this

Thirtieth Day of March, 1999

Attest:

Q. TODD DICKINSON

*Attesting Officer*    *Acting Commissioner of Patents and Trademarks*